United States Patent [19]
Cho et al.

[11] Patent Number: 5,939,310
[45] Date of Patent: Aug. 17, 1999

[54] CULTIVATION OF PAECILOMYCES SP. USING SILKWORMS

[75] Inventors: Sae Yun Cho, Suwon; Sang Duk Ji, Inchun; Soo Ho Lim, Suwon, all of Rep. of Korea

[73] Assignee: Republic of Korea represented by Rural Development Administration, Suwon, Rep. of Korea

[21] Appl. No.: 08/985,934

[22] Filed: Dec. 5, 1997

[30] Foreign Application Priority Data

Dec. 5, 1996 [KR] Rep. of Korea ................. 96-62054
Dec. 5, 1996 [KR] Rep. of Korea ................. 96-62055

[51] Int. Cl.$^6$ .................................................. C12M 1/14
[52] U.S. Cl. ................................. 435/254.1; 435/932
[58] Field of Search ............................. 435/254.1, 932

[56] References Cited

FOREIGN PATENT DOCUMENTS 1095103  11/1994  China .

OTHER PUBLICATIONS

Aoki et al., "The pathogenicity to the silkworm and taxonomic consideration on some muscardine fungi", J. Sericult. Sci. Japan, 1975, 44(5), 365–370.

James et al., "Susceptibility of the convergent lady beetle Coleoptera coccinellidae to four entomogenous fungi", Environmental Entomology, 1994, 23(1), 190–192.

Agudelo et al., "Mass production, infectivity and field application studies with the entomogenous fungus, *Paecilomyces farinosus*", Journal of Invertebrate Pathology, 1983, 42, 124–132.

Ndoye M., "Susceptibility to various entomophagous fungi (Fungi Imperfecti) and development of mycosis by Beauveria bassiana in larvae and pupae of Chilo suppressalis", Bull Inst Foundam Afr Noire Ser A Sci Nat, 1977, 39(2), 303–317.

*Primary Examiner*—Irene Marx
*Assistant Examiner*—Vera Afremova
*Attorney, Agent, or Firm*—Foley & Lardner

[57] ABSTRACT

Disclosed herein is a cultivation of Paecilomyces sp. which has various efficacies such as anti-tumor and reinforcement of immunity, but could not be used wide in human because of relatively limited supply. The artificial cultivation of Paecilomyces sp. comprises steps of (a) inoculating a dilution of spores of Paecilomyces sp. diluted with water to a concentration of $10^7 \sim 10^8$ spores/ml into a larva of 4th~5th instar of silkworm at a temperature of 26~30° C. and a humidity of about 90% or more; and (b) inducing fruitbodies of Paecilomyces sp. by maintaining of the larvae at a temperature of 15~30° C. and a humidity of about 90% or more. In particular, *Paecilomyces japonica* (KCCM-10117), Paecilomyces sp. J300 (KCCM-10116) and *Paecilomyces farinosa* (KCCM-10115).

5 Claims, 3 Drawing Sheets

CULTIVATION OF PAECILOMYCES SP. USING SILKWORMS

BACKGROUND OF THE INVENTION

1. Field of the Invention

The present invention relates to a cultivation of Paecilomyces sp.(Chinese name; Tochu-kaso) using silkworm as a host. More particularly, it relates to a cultivation of Paecilomyces sp. which comprises steps of inoculating Paecilomyces sp. into larvae of silkworms and inducing a fruitbody of Paecilomyces sp. therefrom 2. Description of the Related Art Tochu-kaso is a parasitic living fungus on larvae and pupae of insects. Some of them had been used for the medicinal purpose, and are distributed in many countries, for instance, China, Nepal, Japan, South America, Republic of Korea, etc.

A typical infection route of Tochu-kaso is an epidermal infection wherein its conidia are scattered and adhered to an epidermis of a host insect. The adhered conidia are germinated under appropriate temperature and humidity conditions, and penetrates into a body of the insect. And then, its spawn grown within the interior of the insect body induces a fruitbody on the epidermis of insect. The infected insects died.

Its fruitbody consists of petiole and a fruit portion at an end thereof and has a size of 1.5~10 cm. Further, it has filiform, clubbed or cylindrical shapes and various colors such as white, black, red, brown etc., depending on the species.

Tochu-kaso has been known as a medicinal fungus having pharmacodynamic efficacy against various diseases. For example, in China, it has been mentioned as a secret medicine for eternal youth. In addition, it has been reported that it protects the lung and enhances the functioning of the kidney. Further, the "Jungrubonso", Chinese old pharmacopeia, says that various species such as Yongchuso and Ahyangbongchuso are efficacious against various diseases. Also, in Japan, "Bonsosu" (1801) says that Tochu-kaso was sold as a miracle drug against a lung disease and pleurisy.

Recently, many studies have been conducted in order to evaluate pharmacodynamic efficacy of Tochu-kaso shown in these old pharmacopeia. As a result, it was reported that its extract contains substances capable of reinforcing immune system and thereby can promote cellular and humoral immunities and improve a resistance against various tumors and viruses.

A clinical test conducted in Switzerland reported an example wherein a two weeks by administration of extracts of Tochu-kaso into a drug addict patient can protect him from the temptation and adverse effects of the drug. Further, the patient eventually returned to normalcy.

It has also been known to have effectiveness of alleviating fatigue and stress.

Due to various efficacy, many studies have been and are being conducted on Tochu-kaso in order to incorporate its extract into pharmaceutical compositions or drinks. Although 300 or more species are distributed all over the world, due to its small size and lower distribution density compared with the other fungi or medicinal plants, there is a difficulty in obtaining absolute amount required for the establishment of its pharmacological efficacies and a clinical test. In addition, since its efficacy varies largely depending on the species, this difficulty is so much the worse.

Under this circumstance, the present invention studies have been focused on the cultivation thereof. Firstly, they have got informations from the studies on Tochu-kaso species inhabiting in the nature, its host insects, a route of infection and conditions of inducing fruitbody. And then they make a setting of an appropriate host insect and cultivation conditions.

On basis of these informations, they could establish characteristics of Tochu-kaso species.

The present invention is also accomplished as a results of the same research.

Above all, the present inventors selected silkworm as a host insect in the cultivation since its rearing method is well established. Further, since silkworm itself has been used as a medicine stuff, it is believed to be more preferably used as a host insect. Then, they have conducted in order to find Tochu-kaso strains able to use silkworm as a host insect.

As a result, they found that Paecilomyces sp. can use silkworm as a host.

SUMMARY OF THE INVENTION

Thus, an object of the present invention is to provide a cultivation of Paecilomyces sp.

This and other objects can be accomplished by a cultivation comprising steps of (a) inoculating a dilution of spores of Paecilomyces sp. into larvae of 4th~5th instar of silkworms at a temperature of 26~30° C. and a humidity of about 90% or more; and (b) inducing fruitbodies of Paecilomyces sp. by maintaining of the larvae at a temperature of 15~30° C. and a humidity of about 90% or more.

These and other objects and features of the present invention will be apparent to the skilled in the art from the following detailed description.

DETAILED DESCRIPTION OF THE INVENTION

In accordance with the present invention, a cultivation of Paecilomyces sp. comprises steps of;

(a) inoculating a dilution of spores of Paecilomyces sp. into a larva of 4th~5th instar of silkworm at a temperature of 26~30° C. and a humidity of about 90% or more; and (b) inducing fruitbodies of Paecilomyces sp. by maintaining of the larvae at a temperature of 15~30° C. and a humidity of about 90% or more.

Hereinafter, the cultivation according to the present invention will be described in more detail.

The present invention is characterized in selecting silkworm as a host insect in the cultivation. The present invention has been accomplished on basis of investigation over various wild Tochu-kaso whether or not silkworm as a host insect can be infected by the wild Tochu-kaso. The results are shown in Table 1.

TABLE 1

| Strain | Host insect in the wild | Infection of silkworm |
|---|---|---|
| Cordyceps scarabaeicola | Moth of Coleoptera | no |
| Cordyceps pruinosa | Pupa of Diptera | no |
| Cordyceps sphecocephala | Moth of Hymenoptera | no |
| Cordyceps oxycephala | Moth of Hymenoptera | no |
| Cordyceps gracillioides | Larva of Orthoptera | no |
| Paecilomyces japonica | Pupa of Lepidoptera | yes |
| Paecilomyces sp. J300 | Pupa of Lepidoptera | yes |
| Paecilomyces farinosa | Pupa of Lepidoptera | yes |

As shown in Table 1, Tochu-kaso has different host insects depending on its species. Therefore, the present invention is characterized in providing Paecilomyces sp. as a Tochu-kaso capable of using silkworm as a host insect.

Paecilomyces sp. employed in the present invention may include, but not limited thereto, *Paecilomyces japonica*, Paecilomyces sp. J300 and *Paecilomyces farinosa*

Figure 1:
FIG. 1 is a photograph showing wild *Paecilomyces japonica* parasitizing on pupa of Lepidoptera.

In accordance with the present invention, *Paecilomyces japonica* can be provided in large quantities by culturing of the spores of wild type *Paecilomyces japonica* (FIG. 1) gathered in hillock of the Republic of Korea. That is to say, the spores of wild type *Paecilomyces japonica* is inoculated on PDA(Potato Dextrose Agar) medium or uncleaned rice medium and incubated at a temperature of 20~25° C. for 30~40 days for induction of spawn. A parent strain for artificial cultivation is obtained from this induced spawn. The fruitbody of yellow color is obtained from the pupa infected by spray inoculating the spores of parent strain into epidermis of silkworm. *Paecilomyces japonica* obtained thus had been deposited with Korean Culture Collection of Microorganisms (Korean Foundation of Culture Collection), College of Engineering, Yonsei University, Sodaemun gu, Seoul 120–749, Republic of Korea on Nov. 29, 1996 and received an accession number "KFCC-10939". The deposit was converted into the deposit under Budapest Treaty on Nov. 27, 1997 and received an accession number of "KCCM 10117".

Figure 2:
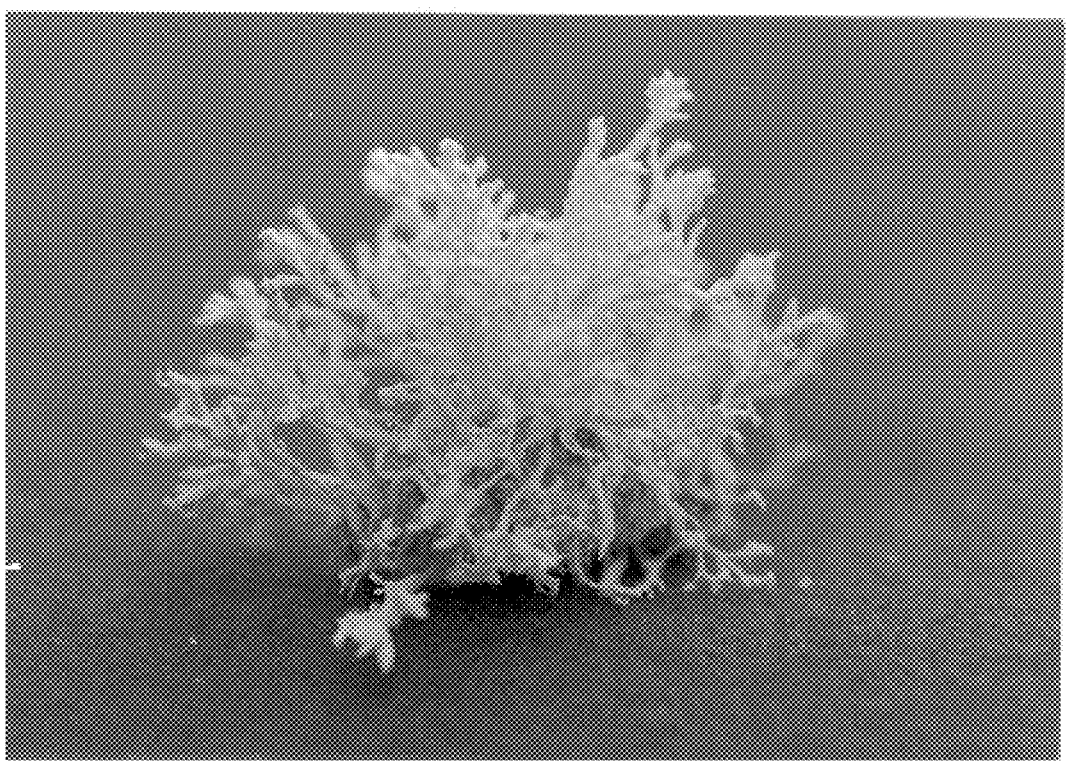
FIG. 2 is a photograph showing *Paecilomyces japonica* cultivated artificially according to the present invention.

*Paecilomyces japonica* (KCCM 10117) is a typical strain belonging to incomplete fungus among thread fungus and has many hosts of various insects. Mainly, it is parasitic on larva and pupa of Lepidoptera and forms a yellow fruitbody having 1~10 of branches like a tree. The size of fruitbody is 1.5~4.7 cm, and white powder-like conidia are present countlessly on a fruit portion (FIG. 2).

Figure 3:
FIG. 3 is a photograph showing wild Paecilomyces sp. J300 parasitizing on pupa of Lepidoptera.
Figure 4:
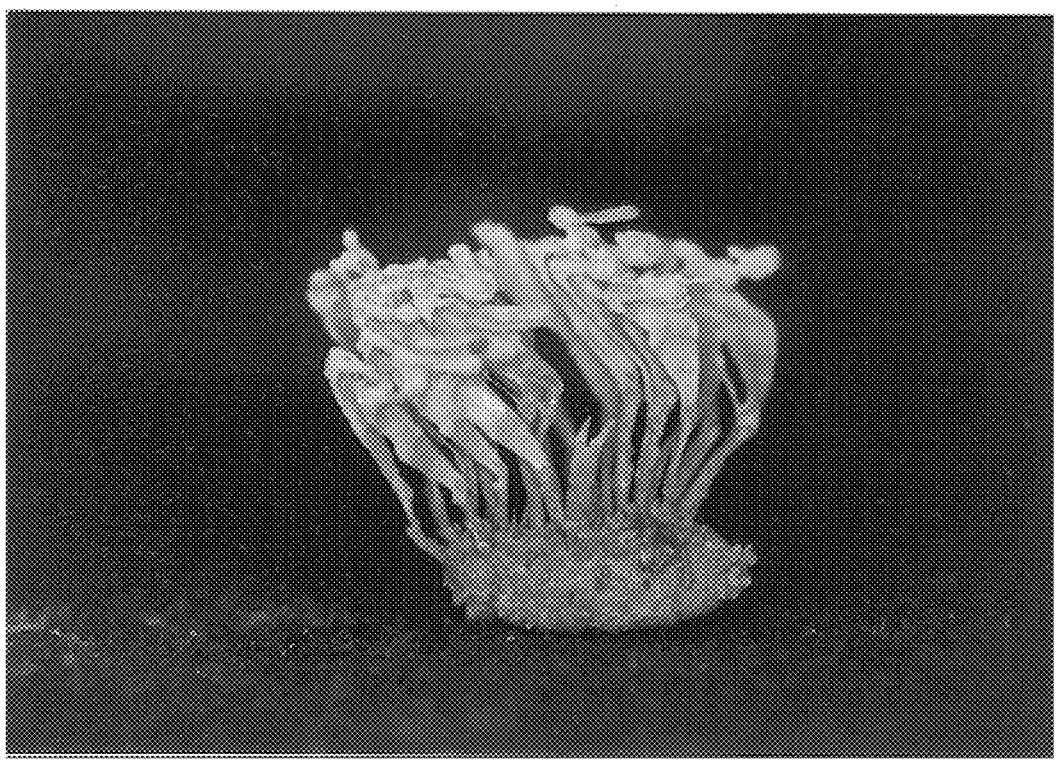
FIG. 4 is a photograph showing Paecilomyces sp. J300 cultivated artificially according to the present invention.

Further, in accordance with the present invention, Paecilomyces sp. J300 can be provided in large quantities by culturing of the spores of wild type Paecilomyces sp. J300 (FIG. 3) gathered in hillock of the Republic of Korea. That is to say, the spores of wild type Paecilomyces sp. J300 is inoculated on PDA(Potato Dextrose Agar) medium or uncleaned rice medium and incubated at a temperature of 20~25° C. for 30~40 days for induction of spawn. A parent strain for artificial cultivation is obtained from this induced spawn. The fruitbody is obtained from the infected pupa by spray inoculating the spores of parent strain into epidermis of silkworm. The fruitbody consists of light brown petiole and white head portion, and its size is 2.0~3.0 cm. Further, a ascocarp on the head portion of the fruitbody is gymnocarpous.

Paecilomyces sp. J300 obtained thus had been deposited with Korean Culture Collection of Microorganisms (Korean Foundation of Culture Collection), College of Engineering, Yonsei University, Sodaemun gu, Seoul 120–749, Republic of Korea on Nov. 29, 1996 and received an accession number "KFCC-10938". The deposit was converted into the deposit under Budapest Treaty on Nov. 27, 1997 and received an accession number of "KCCM 10116".

Paecilomyces sp. J300 (KCCM 10116) is a typical strain belonging to incomplete fungus among thread fungus and has many hosts of various insects. Mainly, it is parasitic on pupa of Lepidoptera.

Figure 5:
FIG. 5 is a photograph showing wild *Paecilomyces farinosa* parasitizing on pupa of Lepidoptera.

Further, in accordance with the present invention, *Paecilomyces farinosa* can be provided in large quantities by culturing of the spores of wild type *Paecilomyces farinosa* (FIG. 5) gathered in hillock of the Republic of Korea. That is to say, the spores of wild type *Paecilomyces farinosa* is inoculated on PDA(Potato Dextrose Agar) medium or uncleaned rice medium and incubated at a temperature of 20~25° C. for 30~40 days for induction of spawn. A parent strain for artificial cultivation is obtained from this induced spawn. The white club-like fruitbody is obtained from the pupa infected by spray inoculating the spores of parent strain into epidermis of silkworm. *Paecilomyces farinosa* obtained thus was deposited with Korean Culture Collection of Microorganisms (Korean Foundation of Culture Collection), College of Engineering, Yonsei University, Sodaemun gu, Seoul 120–749, Republic of Korea on Nov. 27, 1997 under Budapest Treaty and received an accession number of "KCCM 10115".

Figure 6:
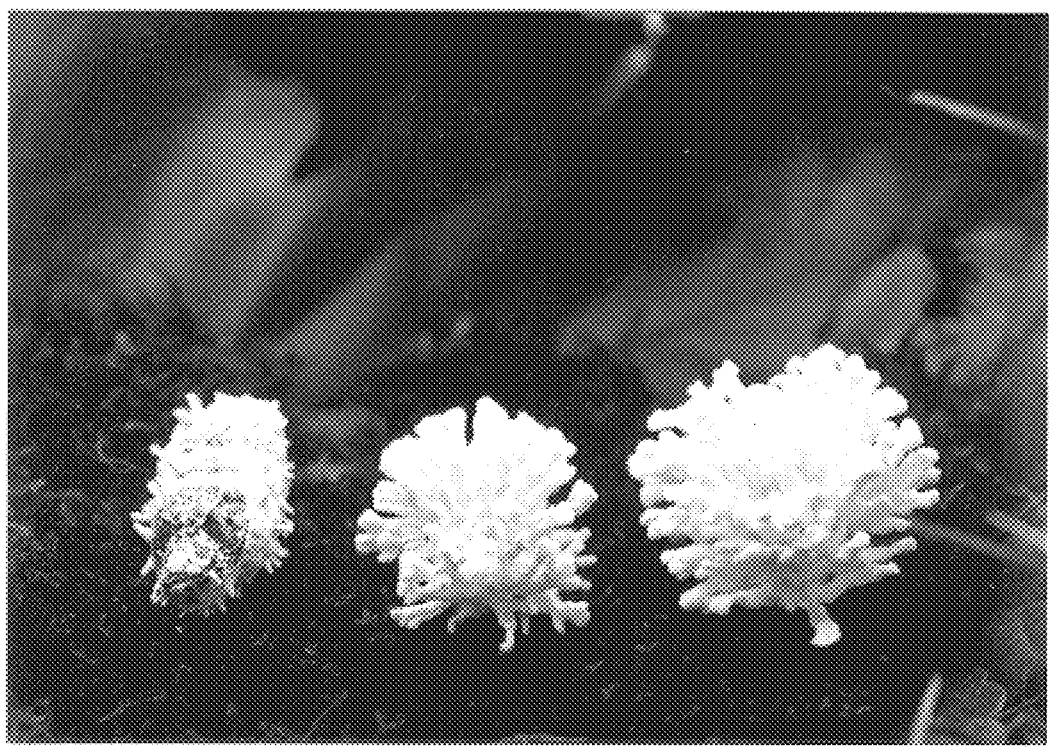
FIG. 6 is a photograph showing *Paecilomyces farinosa* cultivated artificially according to the present invention.

*Paecilomyces farinosa* (KCCM 10115) is a typical strain belonging to incomplete fungus among thread fungus and has many hosts of various insects. Mainly, it is parasitic on larva and pupa of Lepidoptera and forms a white club-like fruitbody. The size of fruitbody is 1.0~2.0 cm, and white powder-like conidia are present countlessly on a fruit portion (FIG. 6).

Paecilomyces sp. can be cultivated artificially using silkworm as a host insect. Therefore, the cultivation of Paecilomyces sp. will be illustrated in more detail by the following description.

First, Paecilomyces sp. is inoculated into the epidermis of silkworm by spraying a dilution of its spores. The dilution is prepared by incubating spores of Paecilomyces sp. on uncleaned rice medium and then diluting with water to a concentration of $10^7$~$10^8$ spores/ml. Then, inoculation is preformed into larva epidermis of 4th~5th instar of silkworm at a temperature 26~30° C. and a humidity of about 90% or more, particularly about 90% for 15~24 hours.

After inoculation, the infected silkworm is reared under a standard condition such as temperature and humidity according to the conventional method, for instance, with feeding mulberry tree leaves to it 2nd~4th in a one day. After 15 days, the infected silkworm is transformed into hardened pupa whose interior is full of the white spawn. The hardened pupa is maintained at a temperature of 15~30° C. and a humidity of about 90% or more, particularly about 90% for inducing of fruitbodies. After 1~5 days, the light white spawn is appeared on the epidermis of pupa. And, after further 1~5 days, the fruitbodies start to be induced. After further 30~40 days, the fruitbodies having average size of 2.0~3.0 cm are obtained.

PREFERRED EMBODIMENTS OF THE INVENTION

The present invention will be illustrated in more detail by way of the following Examples. The following Examples are merely illustrative and it should be understood that the present invention is not limited to these Examples.

EXAMPLE 1

In order to establish inoculating conditions in an artificial cultivation, the infection rate was investigated under various conditions such as concentration, humidity, temperature and instar of silkworm. The results are shown in Table 2 induction rate of fruitbody is most high at 20~26° C. for *Paecilomyces japonica* (KCCM-10117), at 18~24° C. for Paecilomyces sp. J300 (KCCM-10116), and at 15~24° C. for *Paecilomyces farinosa* (KCCM-10115).

TABLE 2

Inoculating condition

| | | | | Host: Silkworm | | | | | |
|---|---|---|---|---|---|---|---|---|---|
| Strain | Inoculation | Humidity | Temperature | 2nd instar | 3rd instar | 4th instar | 5th instar | pupa | moth |
| *Paecilomyces japonica* (KCCM-10117 | Spray inoculation ($10^7$ spores/ml) | 95% | 23~24° C. | — | 9 | 24 | 61 | 58 | — |
| | | | 26~27° C. | 3 | 21 | 46 | 67 | 58 | — |
| | | | 29~30° C. | — | — | 48 | 73 | 62 | — |
| *Paecilomyces sp.* J300 (KCCM-10116 | | | 23~24° C. | — | — | — | 11 | — | — |
| | | | 26~27° C. | — | — | 4 | 41 | 2 | — |
| | | | 29~30° C. | — | — | 5 | 60 | 3 | — |
| *Paecilomyces farinosa* (KCCM-10115 | | | 23~24° C. | — | — | — | 2.0 | — | — |
| | | | 26~27° C. | — | — | — | 5.2 | — | — |
| | | | 29~30° C. | — | — | — | 7.4 | — | — |
| *Paecilomyces japonica* (KCCM-10117 | Spray inoculation ($10^8$ spores/ml) | 95% | 23~24° C. | 1 | 1 | 48 | 82 | 76 | — |
| | | | 26~27° C. | 6 | 6 | 67 | 92 | 81 | — |
| | | | 29~30° C. | — | — | 73 | 98 | 78 | — |
| *Paecilomyces sp.* J300 (KCCM-10116 | | | 23~24° C. | — | — | — | 28 | — | — |
| | | | 26~27° C. | — | 3 | 15 | 62 | 7 | — |
| | | | 29~30° C. | — | 4 | 16 | 89 | 5 | — |
| *Paecilomyces farinosa* (KCCM-10115 | | | 23~24° C. | — | — | 9 | 29 | 6 | — |
| | | | 26~27° C. | — | — | 14 | 46 | 10 | — |
| | | | 29~30° C. | — | — | 19 | 92 | 11 | — |

As shown in Table 2, the infection rate was shown highly when the spores of *Paecilomyces japonica* (KCCM-10117), Paecilomyces sp. J300 (KCCM-10116) or *Paecilomyces farinosa* (KCCM-10115) was inoculated into a larva of 5th instar of silkworm by spraying a dilution of $10^8$ spores/ml at 29~30° C., humidity of 95%.

EXAMPLE 2

In order to establish conditions for inducing fruitbody of Paecilomyces sp., the induction rate and size of fruitbody were measured under various conditions such as temperature and humidity. The results are shown in Table 3.

TABLE 3

| Strain | Temperature (° C.) | Humidity (%) | Induction rate (%) | Size of fruitbody (for 30 days, cm) |
|---|---|---|---|---|
| *Paecilomyces japonica* (KCCM-10117 | 15 | 95 | 88 | 2.0 |
| | 20 | | 95 | 3.7 |
| | 24 | | 95.7 | 5.5 |
| | 26 | | 95 | 3.2 |
| | 30 | | 86 | 1.0 |
| *Paecilomyces sp.* J300 (KCCM-10116 | 15 | 95 | 89 | 0.7 |
| | 18 | | 96 | 1.3 |
| | 20 | | 97.3 | 1.7 |
| | 24 | | 97 | 0.8 |
| | 30 | | 52 | 0.3 |
| *Paecilomyces farinosa* (KCCM-10115 | 15 | 95 | 93.8 | 1.3 |
| | 18 | | 97.9 | 2.0 |
| | 24 | | 92.0 | 1.5 |
| | 27 | | 49.0 | 0.8 |
| | 30 | | 14.3 | 0.4 |

As shown in Table 3, the fruitbody was induced from the pupa when the pupa infected with Paecilomyces sp. was maintained at 29~30° C., humidity of 95%. In particular, the The longer term the infected pupa is maintained for, the bigger size of fruitbody is obtained. However, it is preferable to harvest the fruitbody after it was maintained for 20~40 days, since its weight is reduced by nutrition loss of the pupa and freshness is fallen by excessive growth.

Paecilomyces sp. cultivated artificially according to the present invention induces many fruitbodies compared with wild Paecilomyces sp. Therefore, the mass production of Paecilomyces sp. is possible. Moreover, since Paecilomyces sp. has various pharmacodynamic efficacies, mass supply of Paecilomyces sp. according to the present invention is expected to attribute to promotion of people's health and development of physical strength.

What is claimed is:

1. A method of cultivating Paecilomyces sp., comprising:

(a) inoculating by spraying a dilution of spores of a strain of Paecilomyces sp. selected from the group consisting of *Paecilomyces japonica* (KCCM-10117), Paecilomyces sp. J300 (KCCM-10116) and *Paecilomyces farinosa* (KCCM-10115) into a larva of 4th or 5th instar of silkworm at a temperature of 26 to 30° C. and a humidity of about 90% or more;

(b) obtaining the hardened pupa by rearing said larva; and (c) inducing fruitbodies of Paecilomyces sp. by maintaining said pupa at a temperature of 15 to 30° C. and a humidity of about 90% or more.

2. The method according to claim 1, wherein said dilution is prepared by diluting spores of Paecilomyces sp. with water to a concentration of $10^7$ to $10^8$ spores/ml.

3. The method according to claim 1, wherein said Paecilomyces sp. is *Paecilomyces japonica* (KCCM-10117), and wherein said step (a) is performed on a larva of 5th instar of silkworm with a dilution containing about $10^8$ spores/ml, and said step (c) is performed under a temperature of 20 to 26° C. and a humidity of about 95%.

4. The method according to claim 1, wherein said Paecilomyces sp. is Paecilomyces sp. J300 (KCCM-10116), and wherein said step (a) is performed on a larva of 5th instar of silkworm with a dilution containing about $10^8$ spores/ml, and said step (c) is performed under a temperature of 18 to 24° C. and a humidity of about 95%.

5. The method according to claim 1, wherein said Paecilomyces sp. is *Paecilomyces farinosa* (KCCM-10115), and wherein said step (a) is performed on a larva of 5th instar of silkworm with a dilution containing about $10^8$ spores/ml, and said step (c) is performed under a temperature of 15 to 24° C. and a humidity of about 95%.

* * * * *